US012599346B2

(12) United States Patent
Miyazaki

(10) Patent No.: US 12,599,346 B2
(45) Date of Patent: Apr. 14, 2026

(54) PHOTON COUNTING COMPUTED TOMOGRAPHY APPARATUS AND PHOTON-COUNTING CT-SCANNING CONDITION SETTING METHOD

(71) Applicant: CANON MEDICAL SYSTEMS CORPORATION, Otawara (JP)

(72) Inventor: Hiroaki Miyazaki, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 156 days.

(21) Appl. No.: 18/524,076

(22) Filed: Nov. 30, 2023

(65) Prior Publication Data

US 2024/0180503 A1 Jun. 6, 2024

(30) Foreign Application Priority Data

Dec. 5, 2022 (JP) ................................. 2022-194288

(51) Int. Cl.
| | |
|---|---|
| *A61B 6/00* | (2024.01) |
| *A61B 6/03* | (2006.01) |
| *A61B 6/42* | (2024.01) |
| *A61B 6/46* | (2024.01) |

(52) U.S. Cl.
CPC .............. *A61B 6/4241* (2013.01); *A61B 6/03* (2013.01); *A61B 6/465* (2013.01)

(58) Field of Classification Search
None
See application file for complete search history.

(56) References Cited

U.S. PATENT DOCUMENTS

| | | |
|---|---|---|
| 2016/0033654 A1 | 2/2016 | Tamura et al. |
| 2016/0262713 A1* | 9/2016 | Flohr ................... A61B 6/5205 |
| 2017/0238896 A1* | 8/2017 | Iwai ..................... A61B 6/4035 |
| 2018/0236267 A1 | 8/2018 | Kuang et al. |

FOREIGN PATENT DOCUMENTS

| | | |
|---|---|---|
| JP | 2006-101926 A | 4/2006 |
| JP | 2014-14445 A | 1/2014 |
| JP | 2016-32635 A | 3/2016 |
| JP | 2017-131336 A | 8/2017 |

OTHER PUBLICATIONS

Extended European Search Report dated Apr. 16, 2024 in corresponding European Patent Application No. 23214034.3, 8 pages.
European Office Action issued Sep. 25, 2025 in European Patent Application No. 23 214 034.3, 5 pgs.

* cited by examiner

*Primary Examiner* — Hoon K Song
(74) *Attorney, Agent, or Firm* — Oblon, McClelland, Maier & Neustadt, L.L.P.

(57) ABSTRACT
A photon counting computed tomography apparatus according to an embodiment includes processing circuitry and a display. The processing circuitry is configured to set a scanning condition required in photon counting CT scanning based on the imaging mode related to photon counting CT scanning or based on the examination objective of performing the photon counting CT scanning of a subject. The display is configured to display the set scanning conditions.

13 Claims, 4 Drawing Sheets

CMI

FIG.4

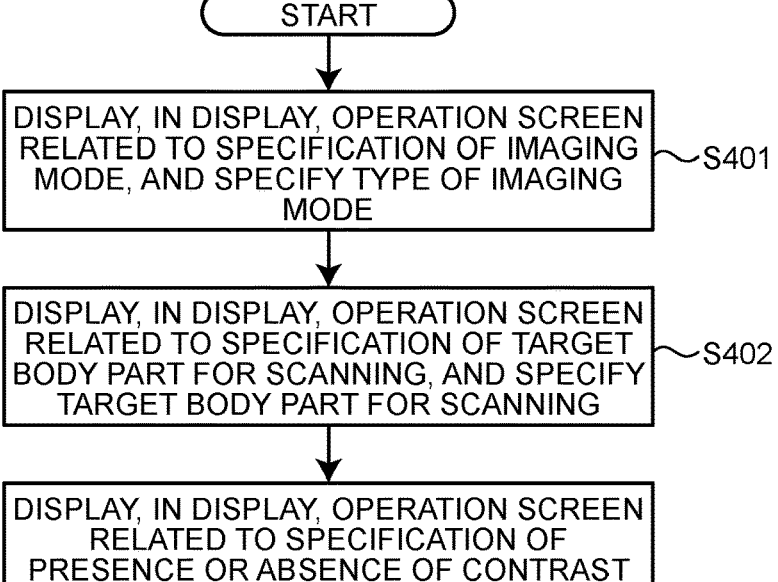

```
                    ┌──────────┐
                    │  START   │
                    └────┬─────┘
                         │
                         ▼
┌────────────────────────────────────────┐
│ DISPLAY, IN DISPLAY, OPERATION SCREEN   │
│ RELATED TO SPECIFICATION OF IMAGING     │──S401
│ MODE, AND SPECIFY TYPE OF IMAGING       │
│ MODE                                    │
└────────────────────┬───────────────────┘
                     │
                     ▼
┌────────────────────────────────────────┐
│ DISPLAY, IN DISPLAY, OPERATION SCREEN   │
│ RELATED TO SPECIFICATION OF TARGET      │──S402
│ BODY PART FOR SCANNING, AND SPECIFY     │
│ TARGET BODY PART FOR SCANNING           │
└────────────────────┬───────────────────┘
                     │
                     ▼
┌────────────────────────────────────────┐
│ DISPLAY, IN DISPLAY, OPERATION SCREEN   │
│ RELATED TO SPECIFICATION OF            │
│ PRESENCE OR ABSENCE OF CONTRAST        │
│ AGENT AND TYPE OF CONTRAST AGENT,      │──S403
│ AND SPECIFY PRESENCE OR ABSENCE        │
│ OF CONTRAST AGENT AND TYPE OF          │
│ CONTRAST AGENT                         │
└────────────────────┬───────────────────┘
                     │
                     ▼
┌────────────────────────────────────────┐
│ COLLATE TYPE OF IMAGING MODE,          │
│ TARGET BODY PART FOR SCANNING,         │
│ PRESENCE OR ABSENCE OF CONTRAST        │──S404
│ AGENT, AND TYPE OF CONTRAST AGENT      │
│ WITH LOOK UP TABLES, AND SET           │
│ SCANNING CONDITIONS                    │
└────────────────────┬───────────────────┘
                     │
                     ▼
┌────────────────────────────────────────┐
│ GENERATE IMAGING PROTOCOL USING        │
│ SCANNING CONDITIONS, AND DISPLAY       │──S405
│ SCANNING CONDITIONS AND IMAGING        │
│ PROTOCOL                               │
└────────────────────┬───────────────────┘
```

S406

IS IMAGING PROTOCOL FINALIZED?          NO

YES

S407

ACCORDING TO INSTRUCTION FROM OPERATOR, EDIT AT LEAST EITHER SCANNING CONDITIONS OR IMAGING PROTOCOL, AND DISPLAY EDITED IMAGING PROTOCOL AND/OR EDITED SCANNING CONDITIONS

END

PHOTON COUNTING COMPUTED TOMOGRAPHY APPARATUS AND PHOTON-COUNTING CT-SCANNING CONDITION SETTING METHOD

CROSS-REFERENCE TO RELATED APPLICATIONS

This application is based upon and claims the benefit of priority from Japanese Patent Application No. 2022-194288, filed on Dec. 5, 2022, the entire contents of which are incorporated herein by reference.

FIELD

Embodiments described herein relate generally to a photon counting computed tomography apparatus and a photon-counting CT-scanning condition setting method.

BACKGROUND

For example, prior to performing computed tomography (CT) scanning using a photon counting computed tomography (PCCT) apparatus, various settings (hereinafter, called radiographic condition settings) are performed. For example, the setting of the radiographic conditions (such as the X-ray tube voltage and the X-ray tube current) is performed based on the target body part for radiography and/or based on the body type of the subject, and the setting of the energy bins (the energy ranges) specific to the PCCT apparatus is performed.

In a PCCT apparatus, the image reconstruction (imaging) modes include: a counting mode that is a non-photon-counting mode for achieving images close to CT images; a generation/display mode for generating and displaying material decomposition images; and virtual monochromatic X-ray images mode. Thus, for each objective regarding an imaging mode, it is assumed that the most suitable radiographic conditions are set. There are times when the most suitable radiographic conditions according to the objective regarding an imaging mode become complicated. Hence, setting the most suitable radiographic conditions is sometimes a difficult task.

BRIEF DESCRIPTION OF THE DRAWINGS

FIG. 4 is a flowchart for explaining an example of the sequence of operations in a scanning condition setting operation according to the embodiment.

DETAILED DESCRIPTION

Figure 1:
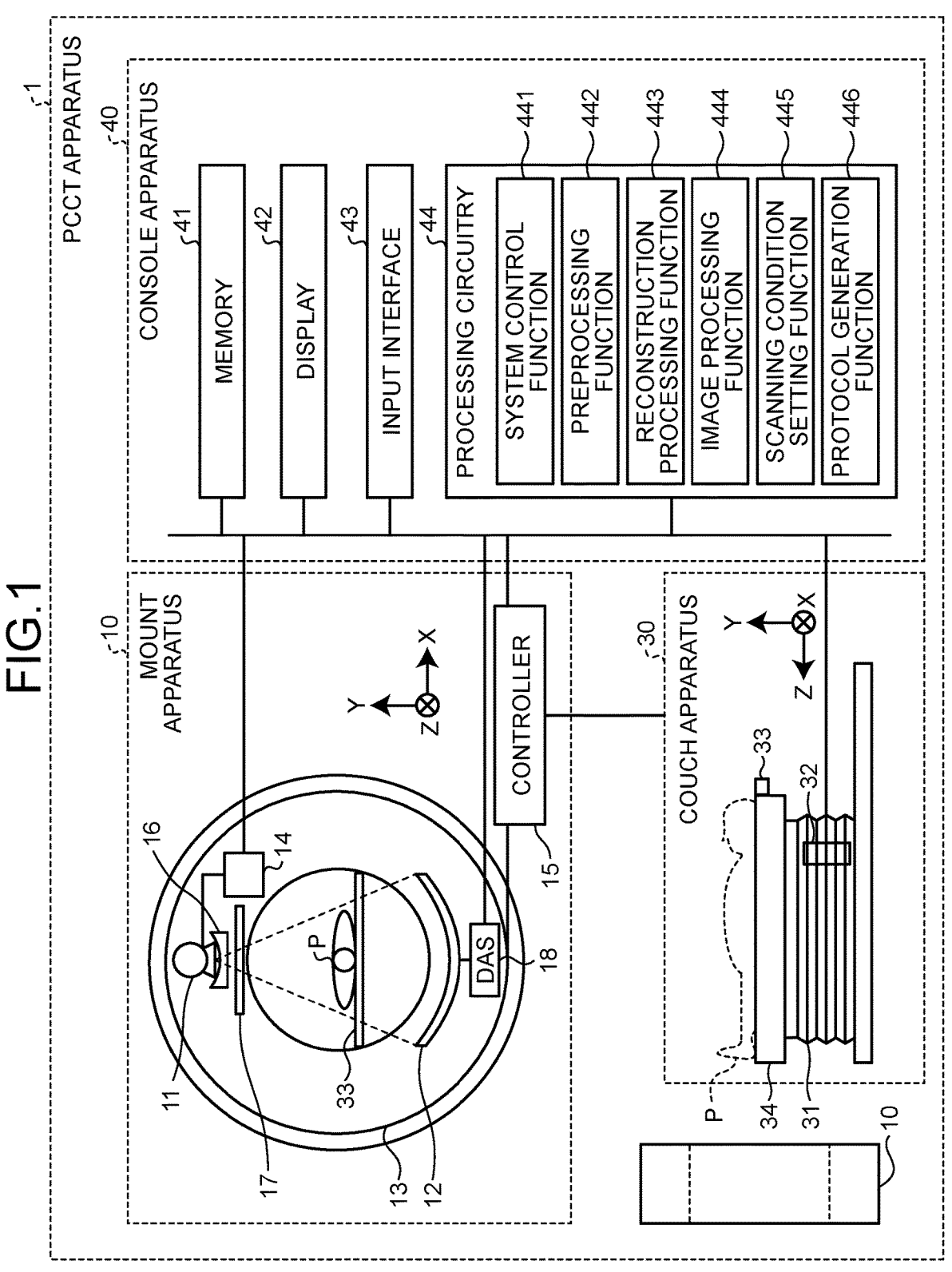
FIG. 1 is a diagram illustrating an exemplary configuration of a PCCT apparatus according to an embodiment.

An object of embodiments disclosed in this specification and the accompanying drawings is ensured that the radiographic conditions are set in the most suitable manner in the CT examination performed using the photon counting computed tomography apparatus, although it is not construed as limiting. Other objects corresponding to the effects of the respective elements specified in the following embodiments may be conceivable.

A photon counting computed tomography apparatus according to an embodiment includes processing circuitry and a display. The processing circuitry is configured to set a scanning condition required in photon counting CT scanning based on the imaging mode related to photon counting CT scanning or based on the examination objective of performing the photon counting CT scanning of a subject. The display is configured to display the set scanning conditions.

An exemplary embodiment of a photon counting computed tomography (PCCT) apparatus and a photon-counting CT-scanning condition setting method is described below with reference to the accompanying drawings. In the embodiment, the constituent elements having the same reference numerals assigned thereto are assumed to perform identical operations, and the same explanation about them is not given in a repeated manner. The photon-counting CT-scanning condition setting method according to the embodiment can be implemented using various types of server apparatuses. In other words, the photon-counting CT-scanning condition setting method according to the embodiment can be implemented in any server apparatus that is capable of executing a photon-counting CT-scanning condition setting program.

Meanwhile, the apparatus capable of implementing the technical features according to the present embodiment is not limited to a PCCT apparatus. Alternatively, for example, it is possible to use a multifunction apparatus configured using a nuclear medicine diagnostic apparatus, such as a positron emission tomography (PET) apparatus or a single photon emission computed tomography (SPECT) apparatus, in combination with a PCCT apparatus.

Embodiment

FIG. 1 is a diagram illustrating an exemplary configuration of a PCCT apparatus 1 according to the embodiment. The PCCT apparatus 1 includes a mount apparatus 10 that is also called a gantry; a couch apparatus 30; and a console apparatus 40. If the technical features according to the present embodiment are to be implemented using a scanning condition setting apparatus, then the scanning condition setting apparatus is equivalent to a configuration obtained when, for example, a system control function 441, a preprocessing function 442, a reconstruction processing function 443, and an image processing function 444 of the console apparatus 40 illustrated in FIG. 1 are left out. Thus, the scanning condition setting apparatus can be implemented by leaving out unwanted constituent elements from among the constituent elements of the console apparatus 40 illustrated in FIG. 1.

In the present embodiment, the longitudinal direction of the rotation axis of a rotatable frame 13 in the non-tilted state is defined as the Z-axis direction; the direction that is orthogonal to the Z-axis direction and that is oriented from the center of rotation toward a columnar support meant for supporting the rotatable frame 13 is defined as the X-axis direction; and the direction that is orthogonal to the Z-axis direction and the X-axis direction is defined as the Y-axis direction. Meanwhile, in FIG. 1, a plurality of mount apparatuses 10 is illustrated for explanatory convenience. However, in the actual configuration of the PCCT apparatus 1, only a single mount apparatus 10 is present.

The mount apparatus 10 and the couch apparatus 30 operate either based on an operation performed by an operator using the console apparatus 40 or based on an operation performed by an operator using an operating unit provided in the mount apparatus 10 or the couch apparatus 30. Herein, the operator implies, for example, a doctor, a radiology technologist, or a service person doing the servicing of the PCCT apparatus 1. The mount apparatus 10, the couch apparatus 30, and the console apparatus 40 are communicably connected to each other in a wired manner or a wireless manner.

The mount apparatus 10 includes an imaging system that bombards X-rays onto a subject P and collects projection data from the detection data about the X-rays that have passed through the subject P. The mount apparatus 10 includes an X-ray tube 11, an X-ray detector 12, the rotatable frame 13, an X-ray high-voltage generator 14, a controller 15, a wedge 16, a collimator 17, and a data acquisition system (DAS) 18.

The X-ray tube 11 is a vacuum tube that receives the application of a high voltage as well as receives the supply of a filament current from the X-ray high-voltage generator 14, and that generates X-rays by bombarding thermal electrons from a cathode (filament) to an anode (target). When the thermal electrons collide with the target, it results in the generation of X-rays. The X-rays generated at the tube focal position in the X-ray tube 11 pass through an X-ray radiation window formed in the X-ray tube 11; become formed in, for example, a cone-beam shape via the collimator 17; and are bombarded onto the subject P. For example, the X-ray tube 11 can be a rotating anode X-ray tube in which X-rays are generated by bombarding thermal electrons onto a rotating anode.

The X-ray detector 12 detects the photons of the X-rays that are generated in the X-ray tube 11. More particularly, the X-ray detector 12 detects, in units of photons, the X-rays that were bombarded from the X-ray tube 11 and that have passed through the subject P; and outputs, to the DAS 18, an electrical signal corresponding to the X-ray dosage. That is, the X-ray detector 12 is implemented using an X-ray detector of the photon counting type. The X-ray detector 12 includes, for example, a plurality of detection element arrays in each of which a plurality of detection elements (also called X-ray detection elements) is arranged in the fan-angle direction (also called the channel direction) along a single circular arc centered on the focal point of the X-ray tube 11. In the X-ray detector 12, the detection element arrays are flatly arranged along the Z-axis direction. That is, for example, the X-ray detector 12 has a structure in which a plurality of detection element arrays is flatly arranged along the cone-angle direction (also called the row direction or the slice direction).

Meanwhile, the PCCT apparatus 1 can be of various types, such as the rotate/rotate-type (third generation CT) in which the X-ray tube 11 and the X-ray detector 12 rotate as a single unit around the subject P, or the stationary/rotate-type (fourth generation CT) in which a large number of X-ray detection elements arrayed in a ring-like manner are kept fixed and only the X-ray tube 11 rotates around the subject P. Any type of the PCCT apparatus 1 is applicable in the present embodiment.

The X-ray detector 12 is of the direct conversion type and includes a semiconductor apparatus for converting the incident X-rays into an electrical charge. The X-ray detector 12 according to the present embodiment includes, for example, at least a single high-voltage electrode, at least a single semiconductor crystal, and a plurality of read-out electrodes. The semiconductor apparatus is also called an X-ray converter. The semiconductor crystal is implemented using, for example, cadmium telluride (CdTe) or cadmium zinc telluride (CdZnTe). In the X-ray detector 12, electrodes are disposed on the two surfaces that are opposite to each other across the semiconductor crystals and that are orthogonal to the Y direction. That is, in the X-ray detector 12, a plurality of anode electrodes (also called read-out electrodes or pixel electrodes) is placed opposite to a cathode electrode (also called a common electrode) across the semiconductor crystals.

In between the read-out electrodes and the common electrodes, a bias voltage is applied. In the X-ray detector 12, when the X-rays get absorbed in the semiconductor crystals, electron-hole pairs are generated and the electrons move toward the anodes (toward the anode electrodes (read-out electrodes)), and the positive holes move toward the cathode (toward the cathode electrode). As a result, a signal related to the detection of the X-rays is output from the X-ray detector 12 to the DAS 18.

Meanwhile, the X-ray detector 12 can also be of the indirect conversion type in which the incident X-rays are converted into electrical signals in an indirect manner. Herein, the X-ray detector 12 represents an example of an X-ray detecting unit.

The rotatable frame 13 is an annular frame that supports the X-ray tube 11 and the X-ray detector 12 opposite to each other and that rotates the X-ray tube 11 and the X-ray detector 12 under the control of the controller 15 (explained later). Meanwhile, in addition to including and supporting the X-ray tube 11 and the X-ray detector 12, the rotatable frame 13 also includes and supports the X-ray high-voltage generator 14 and the DAS 18. The rotatable frame 13 is rotatably supported by the non-rotatable portion of the mount apparatus 10 (for example, by a fixed frame (not illustrated in FIG. 1)). Herein, the rotation mechanism includes, for example, a motor that generates a rotary driving force and a bearing that transmits the rotary driving force to the rotatable frame 13 and causes the rotatable frame 13 to rotate. The motor is disposed in, for example, the non-rotatable portion. The bearing is physically connected to the rotatable frame 13 and the motor, and causes the rotatable frame 13 to rotate according to the torque of the motor.

In the rotatable frame 13 as well as in the non-rotatable portion, communication circuitry is disposed that is either of the contactless type or of the contact type. As a result, the units that are supported by the rotatable frame 13 can communicate with the non-rotatable portion or with external apparatuses of the mount apparatus 10. For example, when optical communication is implemented as the contactless communication method, the detection data generated by the DAS 18 is sent using optical communication from a transmitter, which is disposed in the rotatable frame 13 and which includes a light emitting diode (LED), to a receiver, which includes a photodiode and which is disposed in the non-rotatable portion of the mount apparatus 10. Moreover, the detection data is transferred from the non-rotatable portion to the console apparatus 40 using a transmitter. Meanwhile, as the communication method, it is possible to implement contactless data transfer using the capacitive coupling method or the radio wave method, or it is possible to implement a contact-type data transmission method using a slip ring and an electrode brush. Herein, the rotatable frame 13 represents an example of a rotor.

The X-ray high-voltage generator 14 includes electrical circuitry such as a transformer and a rectifier. The X-ray high-voltage generator 14 also includes a high-voltage generator having the function of generating a high voltage to be applied onto the X-ray tube 11 and generating a filament current to be supplied to the X-ray tube 11, and includes an X-ray controller for controlling the output voltage according to the X-rays bombarded from the X-ray tube 11. The high-voltage generator can be of the transformer type or the inverter type. Meanwhile, the X-ray high-voltage generator 14 either can be disposed in the rotatable frame 13, or can be disposed in the fixed frame of the mount apparatus 10. The X-ray high-voltage generator 14 represents an example of an X-ray high-voltage generating unit.

The controller 15 includes processing circuitry having a central processing unit (CPU), and includes a driving mechanism including a motor and an actuator. As far as the hardware resources are concerned, the processing circuitry includes a processor such as a CPU or a micro processing unit (MPU), and includes a memory such as a read only memory (ROM) or a random access memory (RAM). Alternatively, the controller 15 can be implemented using, for example, a processor such as a graphics processing unit (GPU), or an application specific integrated circuit (ASIC), or a programmable logic device (for example, a simple programmable logic device (SPLD), or a complex programmable logic device (CPLD), or a field programmable gate array (FPGA)).

For example, if the processor is a CPU, then it reads the computer programs stored in the memory and executes them to implement the functions. On the other hand, if the processor is an ASIC; then, instead of storing computer programs in the memory, the concerned functions are directly embedded as logic circuitry in the circuitry of the processor. Meanwhile, a processor according to the present embodiment is not limited to be configured as individual circuitry. Alternatively, a plurality of independent circuitry can be combined to constitute a single processor, and the functions can be implemented therein. Moreover, a plurality of constituent elements can be integrated into a single processor and their functions can be implemented in that processor.

The controller 15 receives an input signal from an input interface that is attached to the console apparatus 40 or the mount apparatus 10, and accordingly controls the operations of the mount apparatus 10 and the couch apparatus 30. For example, the controller 15 receives an input signal and performs control to rotate the rotatable frame 13, or performs control to tilt the mount apparatus 10, or performs control to operate the couch apparatus 30 and a couchtop 33. Regarding the control for tilting the mount apparatus 10, according to inclination angle (tilt angle) information input via the input interface attached to the mount apparatus 10, the controller 15 rotates the rotatable frame 13 around the axis parallel to the X-axis direction. Meanwhile, according to the scanning conditions set by a scanning condition setting function 445 (explained later) and/or according to an imaging protocol generated by a protocol generation function (explained later), the controller 15 controls various constituent elements of the mount apparatus 10 and the couch apparatus 30 in regard to performing photon counting CT scanning. In the photon counting CT scanning, unlike the conventional integral type CT scanning, for example, the photons are counted one by one.

The controller 15 either can be disposed in the mount apparatus 10, or can be disposed in the console apparatus 40. Meanwhile, instead of storing computer programs in the memory, they can be directly incorporated in the circuitry of the processor of the controller 15. Herein, the controller 15 represents an example of a control unit.

The wedge 16 is a filter for adjusting the X-ray dosage of the X-rays that are bombarded from the X-ray tube 11. More particularly, the wedge 16 is a filter that transmits and attenuates the X-rays, which are bombarded from the X-ray tube 11, in such a way that the X-rays bombarded from the X-ray tube 11 onto the subject P have a predetermined distribution. For example, the wedge 16 is a wedge filter or a bow-tie filter, and is manufactured by processing aluminum to achieve a predetermined target angle and a predetermined thickness.

The collimator 17 is a lead plate meant for limiting the X-rays, which have passed through the wedge 16, within an X-ray bombardment range, and constitutes a slit because of a combination of a plurality of lead plates. The collimator 17 is sometimes also called an X-ray limiter.

The data acquisition system (DAS) includes a plurality of scaling circuitry, each of which includes an amplifier for performing amplification with respect to the electrical signal output from each detection element of the X-ray detector 12, includes an A/D converter for converting the amplified electrical signals into digital signals, and generates detection data representing the result of a counting operation performed using the detection signal obtained the X-ray detector 12. The result of the counting operations represents data that is assigned with the number of photons of the X-rays in each energy bin. Herein, an energy bin is equivalent to an energy region having a predetermined width. For example, the DAS 18 counts the photons originating from the X-rays that were bombarded from the X-ray tube 11 and that have passed through the subject P (i.e., counts the X-ray photons), and generates, as the detection data, the result of the counting operation in which the energy of the counted photons is discriminated. Meanwhile, the DAS 18 represents an example of a data collecting unit.

The detection data generated by the DAS 18 is transferred to the console apparatus 40. The detection data represents the following set of data: the channel number of the detector pixels that generated the detection data; the row number of the detector pixels; the view numbers indicating the collected views (also called the projection angles); and the value indicating the detected X-ray dosage. Meanwhile, as the view angles, it is possible to use the order of collection of the views (the collection timings of the views), or to use the numbers (for example, 1 to 1000) indicating the angles of rotation of the X-ray tube 11. Each of a plurality of counting circuitry in the DAS 18 is implemented using a circuitry family having circuitry elements capable of generating the detection data. In the present embodiment, when simply the term "detection data" is used, it not only includes the meaning of net data that is detected by the X-ray detector 12 and that is not yet subjected to preprocessing, but it also includes the meaning of raw data obtained as a result of performing preprocessing on the net data. Meanwhile, sometimes the data before preprocessing (i.e., the detection data) and the data after preprocessing is collectively referred to as projection data.

The couch apparatus 30 is an apparatus on which the subject P, who is the target for scanning, is made to lie down and is moved. The couch apparatus 30 includes a base 31, a couch driving apparatus 32, the couchtop 33, and a supporting frame 34. The base 31 is a housing that supports the supporting frame 34 to be movable in the vertical direction. The couch driving apparatus 32 is a motor or an actuator that moves the couchtop 33, on which the subject P is lying down, in the long-axis direction of the couchtop 33. The couchtop 33 is a plate placed on the upper surface of the supporting frame 34, and the subject P is asked to lie down on the couchtop 33. Meanwhile, in addition to moving the couchtop 33, the couch driving apparatus 32 can also move the supporting frame 34 in the long-axis direction of the couchtop 33.

The console apparatus 40 includes a memory 41, a display 42, an input interface 43, and processing circuitry 44. Among the memory 41, the display 42, the input interface 43, and the processing circuitry 44; the data communication is performed, for example, via a bus. Herein, the console apparatus 40 is a separate apparatus from the mount apparatus 10. However, alternatively, either the entire console apparatus 40 or some of its constituent elements can be included in the mount apparatus 10.

The memory 41 is implemented, for example, using a semiconductor memory device such as a random access memory (RAM) or a flash memory, or using a hard disk drive (HDD) or a solid state drive (SSD), or using an optical disc. Alternatively, the memory 41 can be a driving apparatus that performs reading and writing of information either with respect to a portable memory medium such as a compact disc (CD), a digital versatile disc (DVD), or a flash memory, or with respect to a semiconductor apparatus such as a random access memory (RAM).

The memory 41 is used to store, for example, the detection data output from the DAS 18, the projection data generated by the preprocessing function 442, and reconstructed images obtained by the reconstruction processing function 443. A reconstructed image represents, for example, three-dimensional CT image data (volume data) or two-dimensional CT image data. Meanwhile, the storage area of the memory 41 can be provided inside the PCCT apparatus 1 or inside an external storage device connected by a network.

The memory 41 is also used to store the scanning conditions set by the scanning condition setting function 445. The scanning conditions represent the imaging conditions used in performing photon counting CT scanning in the PCCT apparatus 1. Regarding a material decomposition mode, examples of the scanning conditions (hereinafter, called discrimination-type scanning conditions) include the X-ray tube voltage, the X-ray tube current, the scanning speed, the total number of energy bins, and the energy range of each of a plurality of energies. Moreover, regarding the counting mode, examples of the scanning conditions (hereinafter, called counting-type scanning conditions) include the X-ray tube voltage and the X-ray tube current corresponding to the integral type CT scanning. Moreover, the counting-type scanning conditions can also include the bin settings such as the total number of energy bins and the energy range of each of a plurality of energies.

The memory 41 is also used to store look up tables (LUTs) of the scanning conditions corresponding to the items in a plurality of elements related to the setting of the scanning conditions. The LUTs are used in the operation for setting the scanning conditions (hereinafter, called a scanning condition setting operation), and are set in advance by a service person or a radiology technologist. Herein, a plurality of elements include, for example, at least two of the following: the type of the imaging mode related to the photon counting CT scanning; the target body part for scanning in the photon counting CT scanning; the presence or absence of a contrast agent; the type of the contrast agent; the X-ray tube voltage; and the material name in the material decomposition mode. However, the elements are not limited to the examples given above. That is, it is also possible to have other elements such as the X-ray tube current, the type of the anticancer drug, and the material name in the anticancer drug.

The imaging modes include a photon counting mode and a material decomposition mode. That is, the items regarding the type of the imaging mode correspond to, for example, the photon counting mode and the material decomposition mode. The photon counting mode is, for example, related to the implementation of a counting operation without discriminating the photon count in any individual energy bin (all energy bins), that is, in a plurality of energy bins, and related to the generation of images without energy discrimination. At that time, the detection data is equivalent to the data in which the counts across all energies are integrated for each channel number, each row number, and each view number. The material decomposition mode is, for example, related to the implementation of a counting operation by discriminating the photon count in a plurality of energy bins, and related to the generation of images accompanied by energy discrimination. At that time, the detection data is equivalent to the data in which the count is indicated for each of a plurality of energy bins in each channel number, each row number, and each view number.

In the photon counting CT scanning, the items regarding the target body part for scanning include, for example, the head region, the chest region, the abdomen, an arm, and a leg. Moreover, the items regarding the presence or absence of a contrast agent include photon counting CT scanning without using a contrast agent and photon counting CT scanning using a contrast agent. Furthermore, the items regarding the type of the contrast agent correspond to the component (iodine, gadolinium, barium sulphate, or gold) included in the contrast agent, such as an iodine series contrast agent, a gadolinium system contrast agent, or a barium sulphate preparation. The items regarding the X-ray tube voltage correspond to, for example, the voltage value of the X-ray tube voltage or the peak X-ray tube voltage (kilovolts peak (kVp)). The material name in the material decomposition mode represents the material name related to the generation of an image suitable for material decomposition. Examples of the material name include water, iodine, gadolinium, gold, and platinum.

Meanwhile, the memory 41 is also used to store an imaging protocol generated by a protocol generation function 446. The imaging protocol includes, for example, photon counting CT scanning corresponding to the scanning conditions set by the scanning condition setting function 445. Moreover, the imaging protocol includes a plurality of types of scanning including the photon count CT scanning, and includes a plurality of scanning conditions corresponding to a plurality of scans. The types of scanning include, for example, scanogram imaging with respect to the subject P, non-contrast-enhanced (non-CE) imaging and/or contrast-enhanced (CE) imaging.

In addition, the imaging protocol includes a plurality of reconstruction conditions corresponding to a plurality of types of scanning. Examples of the reconstruction conditions include a reconstruction function, the presence or absence of image processing, the intensity of various filters related to image processing, and the presence or absence of artifact reduction processing. Meanwhile, with respect to the detection data (such as a projection data constellation) obtained as a result of performing a single photon counting CT scanning, a plurality of reconstruction conditions can be set.

Herein, the scanning conditions and the reconstruction conditions can be collectively referred to as image generation conditions. In this way, the imaging protocol is generated according to, for example, the computed tomography performed on the subject P. Hence, the imaging protocol can be referred to as the scanning plan tailored to the subject P.

The memory 41 is used to store computer programs that are executed by the processing circuitry 44 and that are meant for implementing the system control function 441, the preprocessing function 442, the reconstruction processing function 443, the image processing function 444, the scanning condition setting function 445, and the protocol generation function 446. The memory 41 represents an example of a memory unit.

The display 42 is used to display a variety of information. For example, the display 42 is used to output medical images (CT images) generated by the processing circuitry 44, and to output a graphical user interface (GUI) meant for receiving various operations from the operator. For example, in the display 42, the items in a plurality of elements related to the setting of the scanning conditions are displayed in an operation screen (GUI) in a specifiable manner according to predetermined order.

For example, the display 42 is used to display operation screens related to the specification of the type of the imaging mode, the target body part for scanning, and the presence or absence of a contrast agent and the type of the contrast agent in that order. Moreover, the display 42 is used to display the scanning conditions set by the scanning condition setting function 445 and/or to display the imaging protocol generated by the protocol generation function 446.

As the display 42, for example, it is possible to use a liquid crystal display (LCD), a cathode ray tube (CRT) display, an organic electro luminescence display (OELD), a plasma display, or an arbitrary type of display. Meanwhile, the display 42 can alternatively be disposed in the mount apparatus 10. The display 42 either can be of the desktop type or can be configured with a tablet terminal capable of performing wireless communication with the main body of the console apparatus 40. Herein, the display 42 represents an example of a display unit.

The input interface 43 receives various input operations from the operator, converts the input operations into electrical signals, and outputs the electrical signals to the processing circuitry 44. For example, from the operator, the input interface 43 receives scanning conditions to be implemented at the time of collecting the projection data, or receives the imaging protocol, or receives reconstruction conditions to be implemented at the time of reconstructing the CT image data, or receives image processing conditions related to the postprocessing to be performed with respect to the CT image data. The postprocessing can be performed either in the console apparatus 40 or in an external workstation. Alternatively, the postprocessing can be performed in the console apparatus 40 and a workstation at the same time.

The postprocessing as defined herein represents the concept about the processing to be performed with respect to an image reconstructed by the reconstruction processing function 443. For example, the postprocessing includes multi planar reconstruction (MPR) display of reconstructed images or includes rendering of volume data. Meanwhile, as the input interface 43, it is possible to use, for example, a mouse, a keyboard, a trackball, switches, buttons, a joystick, a touchpad, or a touch-sensitive panel.

However, in the present embodiment, the input interface 43 is not limited to include a physical operating component such as a mouse, a keyboard, a trackball, switches, buttons, a joystick, a touchpad, or a touch-sensitive panel. Alternatively, for example, the input interface 43 can be electric-signal processing circuitry that, from an independentlyinstalled external input apparatus, receives an electric signal corresponding to an input operation, and outputs that electric signal to the processing circuitry 44. The input interface 43 represents an example of an input unit. Meanwhile, the input interface 43 can alternatively be installed in the mount apparatus 10. Moreover, the input interface 43 can be configured with a tablet terminal capable of performing wireless communication with the main body of the console apparatus 40.

The processing circuitry 44 controls the operations of the entire PCCT apparatus 1 according to the electrical signals output from the input interface 43 in regard to the input operations. For example, the processing circuitry 44 includes, as hardware resources, a processor such as a CPU, an MPU, or a GPU, and includes a memory such as a ROM or a RAM. The processing circuitry 44 uses the processor to execute computer programs loaded in its memory and implements the system control function 441, the preprocessing function 442, the reconstruction processing function 443, the image processing function 444, the scanning condition setting function 445, and the protocol generation function 446. Herein, the functions 441 to 446 are implemented in a single processor. However, alternatively, the processing circuitry 44 can be configured by combining a plurality of independent processors, and each processor can be made to execute computer programs and implement the functions 441 to 446.

The system control function 441 controls the functions of the processing circuitry 44 based on the input operations received from the operator via the input interface 43. The system control function 441 reads a control program stored in the memory 41, loads it in the internal memory of the processing circuitry 44, and controls the constituent elements of the PCCT apparatus 1 according to the loaded control program. The system control function 441 represents an example of a system control unit.

The preprocessing function 442 generates projection data as a result performing preprocessing such as logarithmic conversion or offset correction, inter-channel sensitivity correction, and beam hardening correction with respect to the detection data output from the DAS 18. Herein, since the projection data is generated according to known operation details, that explanation is not given again. The preprocessing function 442 represents an example of a preprocessing unit.

The reconstruction processing function 443 performs reconstruction processing with respect to the projection data, which is generated by the preprocessing function 442, using the filtered back projection (FBP) method; and generates CT image data. The reconstruction includes various operations including various correction operations such as scattering correction and beam hardening correction, and including application of a reconstruction function as a reconstruction condition. Meanwhile, the reconstruction performed by the reconstruction processing function 443 is not limited to the FBP method. Alternatively, any other known processing can be implemented, such as successive approximation reconstruction or a deep neural network that outputs a reconstructed image in response to the input of projection data. The reconstruction processing function 443 stores the reconstructed CT image data in the memory 41. The reconstruction processing function 443 represents an example of a reconstruction processing unit.

The reconstruction processing performed by the reconstruction processing function 443 is not limited to generating images based on the pre-reconstruction data such as the projection data, and implies the function of implementing the reconstruction processing in a broad sense. For example, based on the pre-reconstruction data and according to the reconstruction conditions, the reconstruction processing function 443 generates a reference material image, a virtual monochromatic X-ray image, a virtual non-contrast (VNC) image, an iodine map image, an effective atomic number image, an electron density image, and a plurality of energy images.

The reference material image is related to the reference material. Herein, for example, water or iodine represents the reference material. Thus, the reference material image can be, for example, a water image in which the water content (for example, the existence ratio of the water) is expressed on a pixel-by-pixel basis or an iodine image in which the iodine content (for example, the existence ratio of iodine) is expressed on a pixel-by-pixel basis. The virtual monochromatic X-ray image corresponds to monochromatic X-rays that have one particular energy component (keV) in the energy of the X-rays (for example, white radiation) generated in the X-ray tube 11. The virtual monochromatic X-ray image is equivalent to a medical image taken by performing virtual radiography using particular monochromatic X-rays.

A VNC image is generated from, for example, a contrast-enhanced image. An iodine map image is a medical image indicating the degree of staining of the contrast agent that contains iodine as the component. An effective atomic number image is, for example, a medical image that, regarding the types of elements in each of a plurality of voxels, indicates the type of the concerned element when each voxel is configured with only a single element. When each voxel is configured with a plurality of elements, an effective atomic number image represents a medical image indicating the average atomic number. Thus, assuming that a particular voxel is substituted with a single atom, the corresponding atomic number represents the effective atomic number. An effective atomic number image is, for example, equivalent to an image corresponding to characteristic X-rays (k-edge) from among the X-rays generated in the X-ray tube 11.

An electron density image is a medical image indicating the number of electrons estimated to be present in a unit volume. For example, an electron density image corresponds to a medical image indicating the density of the contrast agent. Each of a plurality of energy images corresponds to a medical image generated based on the detection data that is collected for each of a plurality of energy bins in the PCCT apparatus 1. Meanwhile, since the reconstruction processing function 443 can perform reconstruction processing according to known operation details, that explanation is not given again.

The image processing function 444 implements a known method and, based on an input operation received from the operator via the input interface 43, converts the CT image data, which is generated by the reconstruction processing function 443, either into cross-sectional image data of an arbitrary cross-sectional surface or into three-dimensional image data. Meanwhile, the three-dimensional image data can be directly generated by the reconstruction processing function 443 too. Moreover, since the image processing function 444 functions a variety of image processing according to known processing, that explanation is not given again. The image processing function 444 represents an example of an image processing unit.

The scanning condition setting function 445 sets, based on the imaging mode related to the photon count CT scanning, the required scanning conditions in the photon counting CT scanning. For example, the scanning condition setting function 445 uses the imaging mode such as the counting mode or the material decomposition mode as the required condition for setting the scanning conditions, and accordingly sets the scanning conditions related to the photon counting CT scanning. More particularly, the scanning condition setting function 445 sets the scanning conditions using the items in the elements input via an operation screen. For example, only when CT scanning specific to the photon counting CT scanning is to be performed, the scanning condition setting function 445 can be enabled to specify/select the required information for the photon counting CT scanning via an operation screen (GUI) meant for sequentially navigating the operator to set appropriate scanning conditions.

For example, the scanning condition setting function 445 displays, in the display 42, operation screens related to the specification of the type of the imaging mode, the target body part for scanning, and the presence or absence of a contrast agent and the type of the contrast agent in that order. At that time, if the material decomposition mode is specified as the imaging mode and if the presence or absence of a contrast agent and the type of the contrast agent is specified; then, according to the target body part for scanning and according to the presence or absence of a contrast agent and the type of the contrast agent, the scanning condition setting function 445 displays, in the operation screen in the display 42, the number of energy ranges (the bin count) related to the energy discrimination of the photons in the photon counting CT scanning and the energy width in each energy range (energy bin).

If the counting mode is specified as the imaging mode, then the scanning condition setting function 445 displays, in the display 42, operation screens related to the specification of various elements (for example, the target body part for scanning) required in setting the scanning conditions identical to the typical integral type CT scanning. The specification of the target body part for scanning corresponds to the specification of the field of view (FOV). That is, in the counting mode, since the scanning conditions specific to the photon counting CT scanning (for example, the scanning condition such as a plurality of energy ranges) are not required (in the counting mode, the number of bins can be equal to one at the minimum), the scanning condition setting function 445 sets the scanning conditions identical to the usual integral type CT scanning.

When the material decomposition mode is specified as the imaging mode, the scanning condition setting function 445 of the processing circuitry 44 displays, in the display 42, an operation screen for enabling the operator to input the desired material name that is the target for imaging. For example, the scanning condition setting function 445 displays, in the operation screen, the presence or absence of a contrast agent and/or the type of the contrast agent, the target material name for imaging, and the human body structure. According to the specification of the presence or absence of a contrast agent and/or the type of the contrast agent, the target material name for imaging target, and the target body part for scanning; the scanning condition setting function 445 sets the number of energy ranges (i.e., the bin count) and the energy ranges (energy bins) as the scanning condition.

For example, when a gadolinium series contrast agent is selected and/or when gadolinium is specified as the target material name for imaging, the scanning condition setting function 445 sets, for example, the bin count and the width of the energy bins corresponding to a k-edge image related to gadolinium, so that gadolinium can be subjected to imaging. Alternatively, for example, when a gold series contrast agent is selected and/or when gold is specified as the target material name for imaging, the scanning condition setting function 445 sets, for example, the bin count and the width of the energy bins corresponding to a k-edge image related to gold, so that gold can be subjected to imaging. Still alternatively, for example, when an iodine series contrast agent is selected and/or when iodine is specified as the target material name for imaging, the scanning condition setting function 445 sets, for example, the bin count and the width of the energy bins corresponding to a k-edge image related to iodine, so that iodine can be subjected to imaging. At that time, for example, the peak X-ray tube voltage (kVp) is set to be lower than the peak X-ray tube voltage set in the usual CT scanning.

The scanning condition setting function 445 collates the items in a plurality of elements, which is specified and/or selected by the operator, with the look up tables, and sets the scanning conditions corresponding to the photon counting CT scanning. Then, the scanning condition setting function 445 displays the photon counting scanning conditions in the display 42. When the scanning conditions are changed or finalized according to an operator instruction issued via the input interface 43, the scanning condition setting function 445 displays the changed scanning conditions or the finalized scanning conditions in the display 42. For example, in the scanning conditions displayed in the display 42, if the target material name for imaging is changed according to an instruction issued by the operator via the input interface 43, then the scanning condition setting function 445 changes the scanning conditions by referring to the look up table corresponding to the changed material name. Once the scanning conditions are finalized, the scanning condition setting function 445 stores them in the memory 41. The scanning condition setting function 445 represents an example of a scanning condition setting unit.

The protocol generation function 446 uses the scanning conditions set by the scanning condition setting function 445 and generates an imaging protocol that includes the photon counting CT scanning corresponding to the set scanning conditions. The imaging protocol includes a plurality of scanning conditions corresponding to a plurality of types of scanning (scanogram imaging with respect to the subject P, non-contrast-enhanced (non-CE) imaging, and contrast-enhanced (CE) imaging) including the photon counting CT scanning. Prior to the generation of the imaging protocol, the scanning condition setting function 445 sets a plurality of scanning conditions corresponding to a plurality of types of scanning. That is, for each type of scanning, a single scanning condition is set.

Meanwhile, while generating the imaging protocol, the protocol generation function 446 sets the detection data obtained by each of a plurality of types of scanning and sets processing conditions and reconstruction conditions with respect to a variety of data such as the projection data. Prior to the generation of the imaging protocol, for example, according to an instruction issued by the operator via the input interface 43, the protocol generation function 446 sets at least a single processing condition and at least a single reconstruction condition regarding each of a plurality of types of scanning. The protocol generation function 446 represents an example of a protocol generating unit.

The processing conditions are related to, for example, the presence or absence of image processing, the intensity of various filters related to image processing, and the presence or absence of artifact reduction processing. The reconstruction conditions represent the setting of the reconstruction function and the setting of a variety of reconstruction processing (filtered back projection, successive approximation reconstruction, and so on). The reconstruction conditions specific to the photon counting CT scanning are related to a variety of reconstruction according to a reconstruction image specific to the photon counting CT scanning, such as the reference material image, a virtual monochromatic X-ray image, a VNC image, an iodine map image, an effective atomic number image, an electron density image, and a plurality of energy images. Meanwhile, the reconstruction conditions and the processing conditions can be collectively referred to as image generation conditions. Since the processing conditions and the reconstruction conditions conform to known conditions, their explanation is not given herein.

Meanwhile, if the counting mode is selected as the imaging mode and if an integral image corresponding to the energy integral of the detected photons is selected as the reconstruction image to be generated, then the protocol generation function 446 associates the reconstruction conditions, which correspond to the integral image, with the photon counting CT scanning; and incorporates the reconstruction conditions in the imaging protocol. At that time, based on the count data obtained as a result of performing photon counting CT scanning, the reconstruction processing function 443 reconstructs an integral image corresponding to the energy integral of the detected photons. An integral image is different than a counting image and corresponds to a CT image reconstructed by the conventional integral type CT scanning. Regarding the reconstruction conditions related to the reconstruction of an integral image, it is possible to implement a known method. Hence, the explanation about the reconstruction conditions related to the reconstruction of an integral image is not given.

Figure 2:
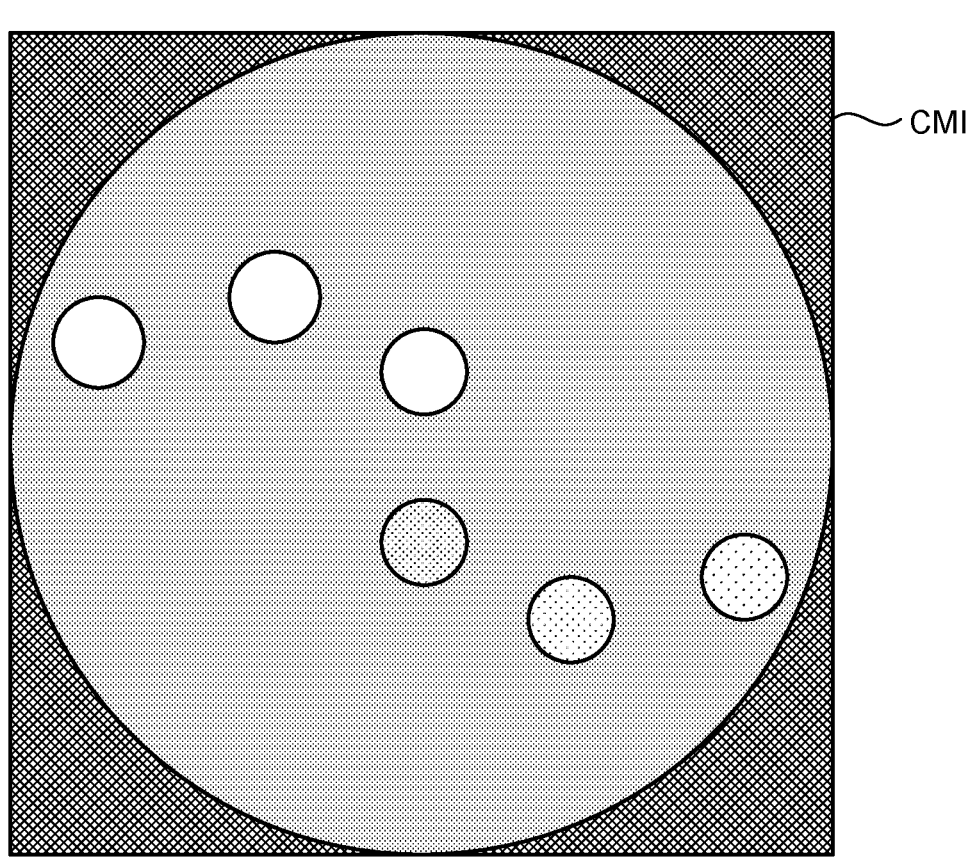
FIG. 2 is a diagram illustrating an example of an integral image generated according to the scanning conditions related to a counting mode according to the embodiment.

FIG. 2 is a diagram illustrating an example of an integral image (also referred to as a counting mode image) CMI generated according to the scanning conditions related to the counting mode. As illustrated in FIG. 2, the integral image CMI is an image equivalent to the CT image reconfigured using the conventional integral type CT scanning. At that time, the peak X-ray tube voltage (kVp) among the scanning conditions is set in an identical manner to the peak X-ray tube voltage in the conventional integral CT scanning.

Figure 3:
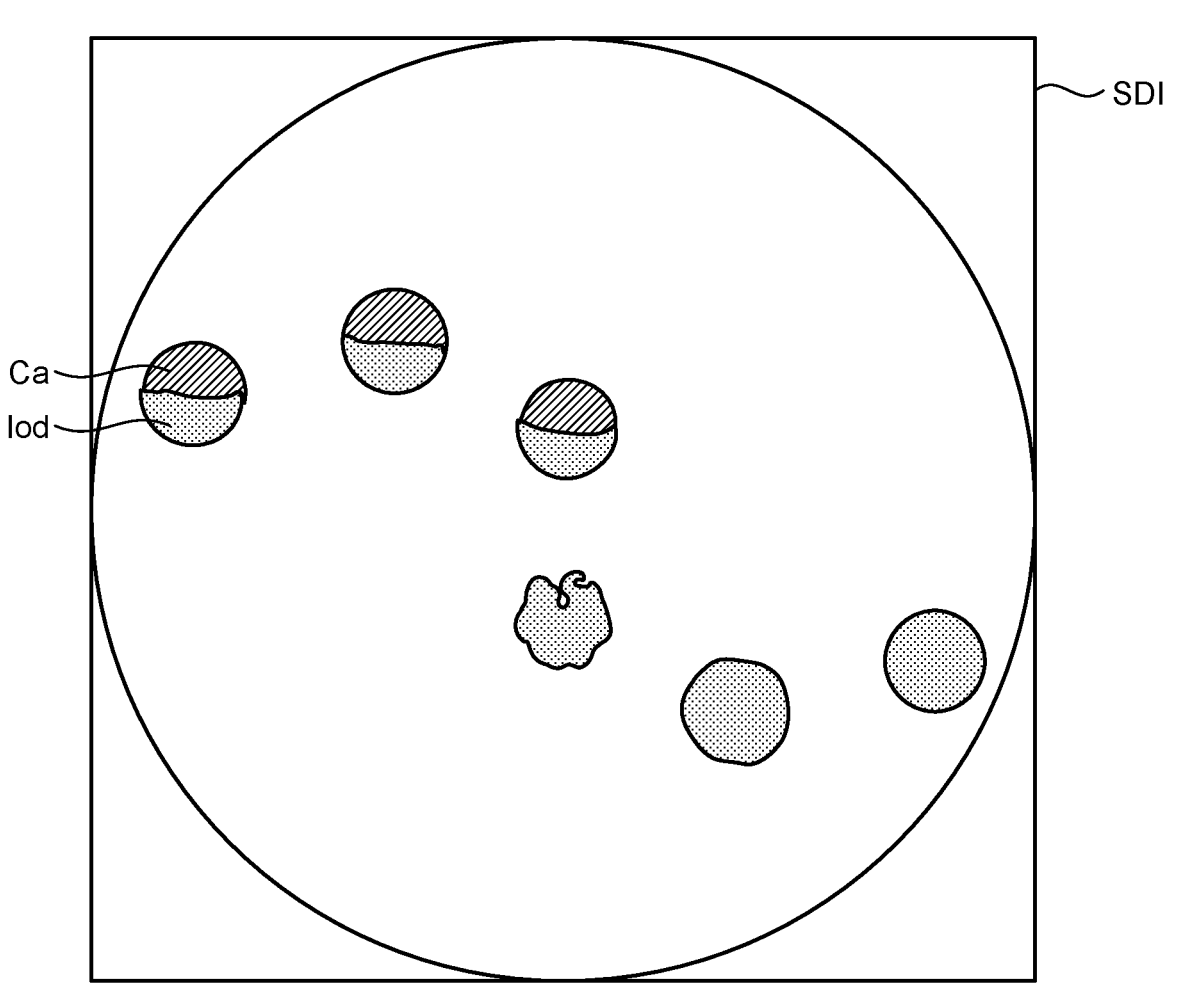
FIG. 3 is a diagram illustrating an example of a material decomposition image generated according to the scanning conditions related to a material decomposition mode according to the embodiment.

FIG. 3 is a diagram illustrating an example of a material decomposition image SDI generated according to the scanning conditions related to the material decomposition mode. In the material decomposition image SD1 illustrated in FIG. 3, iodine Iod and calcium Ca are displayed in different hues (in FIG. 3, different hatching patterns) in the display 42. In the case of decomposing two materials, two or more bins are required as a scanning condition. In the case of focusing on iodine, the peak X-ray tube voltage (kVp) is recommended to be lower than the peak X-ray tube voltage in the conventional integral type CT scanning.

Explained below with reference to FIG. 4 is the scanning condition setting operation performed in the PCCT apparatus 1 configured in the manner explained above according to the present embodiment. FIG. 4 is a flowchart for explaining an example of the sequence of operations in the scanning condition setting operation. In the scanning condition setting operation illustrated in FIG. 4, for explanatory convenience, the generation of the imaging protocol is also included.

Scanning Condition Setting Operation

Step S401

The scanning condition setting function 445 of the processing circuitry 44 displays, in the display 42, an operation screen related to the specification of the imaging mode. Herein, the type of the imaging mode is specified (selected) according to an instruction issued by the operator via the input interface 43. The specified type of the imaging mode is then stored in the memory 41.

Step S402

The scanning condition setting function 445 of the processing circuitry 44 displays, in the display 42, an operation screen related to the specification of the target body part for scanning. Herein, the target body part for scanning is specified (selected) according to an instruction issued by the operator via the input interface 43. The specified target body part for scanning is then stored in the memory 41.

Step S403

The scanning condition setting function 445 of the processing circuitry 44 displays, in the display 42, an operation screen related to the specification of the presence or absence of a contrast agent and the type of the contrast agent. Herein, the presence or absence of a contrast agent is specified (selected) according to an instruction issued by the operator via the input interface 43. The specified presence or absence of a contrast agent is then stored in the memory 41. When the contrast agent is present, the type of the contrast agent is specified (selected) according to an instruction issued by the operator via the input interface 43. The specified type of the contrast agent (the material name included in the contrast agent) is then stored in the memory 41.

Step S404

The scanning condition setting function 445 of the processing circuitry 44 sets the scanning condition by collating the type of the imaging mode, the target body part for scanning, the presence or absence of a contrast agent, the type of the contrast agent, and the look up tables. For example, when the material decomposition mode is the imaging mode, the scanning condition setting function 445 sets, as the scanning conditions, discrimination-type scanning conditions including the X-ray tube voltage, the X-ray tube current, the total number of energy bins, and the energy range of each of a plurality of energies. The energy ranges and the total number of bins are set according to the target body part for scanning and the type of the contrast agent. For example, when a bone represents the target body part for scanning, the energy bins related to imaging are set to have a high level of energy. Alternatively, when the white matter of the brain and/or the gray matter of the brain represents the target body part for scanning, the energy bins related to imaging are set to have a low level of energy.

For example, when gadolinium or gold represents the type of the contrast agent, the energy ranges and the total number of bins are set in a way that is most suitable for the generation of k-edge images according to the concerned element. For example, when a contrast agent containing gadolinium is selected, the energy bins are set on the high-energy side and the low-energy side with reference to the energy of the k-edge of gadolinium. The energy of the k-edge corresponds to the energy of the characteristic X-rays. Meanwhile, when the type of the contrast agent indicates a contrast agent containing iodine, for example, the energy range and the total number of bins are set in a way that is most suitable for the generation of a reference material image having iodine as the reference material. Moreover, if the counting mode is set as the imaging mode, then the scanning condition setting function 445 sets counting-type scanning conditions including the X-ray tube voltage and the X-ray tube current as the scanning conditions. As explained above, the scanning condition setting function 445 sets a plurality of scanning conditions corresponding to a plurality of types of scanning included in the imaging protocol. Meanwhile, the scanning condition setting function 445 can set the X-ray tube voltage, from among the scanning conditions, based on the target body part for scanning and the material name. Moreover, the scanning condition setting function 445 can set the X-ray tube voltage according to the energy related to a virtual monochromatic X-ray image. Furthermore, the scanning condition setting function 445 can set the number of bins and/or the X-ray tube voltage according to the desired amount of noise in the medical images reconstructed by the reconstruction processing function 443.

Step S405

The protocol generation function 446 of the processing circuitry 44 generates the imaging protocol using the scanning conditions. More particularly, while generating the imaging protocol, the protocol generation function 446 sets the processing conditions and the reconstruction conditions with respect to the data obtained as a result of performing photon counting CT scanning.

For example, the protocol generation function 446 sets at least a single processing condition and at least a single reconstruction condition regarding each of a plurality of types of scanning. The setting of the processing conditions and the reconstruction conditions can be done according to a known method. Hence, that explanation is not given again. Then, the protocol generation function 446 uses the scanning conditions, the processing conditions, and the reconstruction conditions that are set, and generates an imaging protocol. At that time, using the scanning conditions, the protocol generation function 446 displays an editing screen in the display 42 for the purpose of editing the imaging protocol.

The editing of the imaging protocol is performed using the editing screen according to an instruction issued by the user via the input interface 43. In the editing screen, a plurality of types of scanning included in the imaging protocol and the set scanning conditions are displayed along with the target scan for editing. When the editing of the imaging protocol is completed, the protocol generation function 446 displays the edited imaging protocol along with the scanning conditions in the display 42. In this way, the imaging protocol gets generated. Meanwhile, when a virtual monochromatic X-ray image is specified as the image to be generated, the scanning condition setting function 445 can set the peak X-ray tube voltage (kVp) according to the energy range (KeV) to be displayed as the virtual monochromatic X-rays.

Step S406

When the finalization of the imaging protocol is input according to an instruction issued by the operator by the input interface 43 (Yes at Step S406), the scanning condition setting operation is ended. At that time, the protocol generation function 446 stores the finalized imaging protocol in the memory 41. However, if the finalization of the imaging protocol is not input according to an instruction issued by the operator by the input interface 43 (No at Step S406), then the operation at Step S407 is performed.

After the scanning condition setting operation is ended, a plurality of types of scanning included in the imaging protocol is implemented according to the scanning conditions in response to an instruction issued by the operator via the input interface 43. Then, with respect to the detection data obtained as a result performing the photon counting CT scanning, preprocessing and reconstruction is performed according to the image generation conditions. As a result, medical images corresponding to a plurality of types of scanning are generated.

Step S407

The protocol generation function 446 of the processing circuitry 44 displays, in the display 42, an editing screen related to the editing of at least either the scanning conditions or the imaging protocol. Herein, according to an instruction issued by the operator via the input interface 43, at least either the scanning conditions or the imaging protocol is edited. At that time, the protocol generation function 446 displays the edited imaging protocol and/or the edited scanning conditions in the display 42. After the operation at Step S407 is performed, the operation at Step S406 is performed again.

In the PCCT apparatus 1 according to the embodiment described above, the scanning conditions required in the photon counting CT scanning are set based on the imaging mode related to the photon counting CT scanning, and the set scanning conditions are displayed. Moreover, in the PCCT apparatus 1 according to the embodiment, the items in a plurality of elements related to the setting of the scanning conditions are displayed in an operation screen in a specifiable manner according to a predetermined order; and the scanning conditions are set using the items in the elements input via the operation screen. For example, in the PCCT apparatus 1 according to the embodiment, the imaging modes include, for example, the photon counting mode and the material decomposition mode, and a plurality of elements implies, for example, at least two of the following: the type of the imaging mode, the target body part for scanning in the photon counting CT scanning, the presence or absence of a contrast agent, the type of the contrast agent, the X-ray tube voltage, and the material name in the material decomposition mode.

Furthermore, in the PCCT apparatus 1 according to the embodiment, operation screens are displayed in regard to the specification of the type of the imaging mode, the target body part for scanning, and the presence or absence of a contrast agent and the type of the contrast agent in that order. Subsequently, if the material decomposition mode is specified as the imaging mode and if the presence or absence of a contrast agent and the type of the contrast agent is specified; then, according to the target body part for scanning and according to the presence or absence of a contrast agent and the type of the contrast agent, the number of energy ranges related to the energy discrimination of the photons in the photon counting CT scanning and the energy width in each energy range (energy bin) is displayed in the operation screen.

As a result, in the PCCT apparatus 1 according to the embodiment, in the case of performing scanning specific to the photon counting CT scanning, the information required for the photon counting CT scanning can be specified and/or selected. Moreover, in the PCCT apparatus 1 according to the embodiment, when the counting mode is set as the imaging mode, a plurality of energy bins cannot be set, thereby making it unnecessary to set the scanning conditions specific to the photon counting CT scanning. Hence, the radiographic conditions required for the usual integral type CT scanning can be set according to, for example, the target body part for scanning. Hence, in the PCCT apparatus 1 according to the embodiment, according to the desired objective of the operator in the photon counting CT scanning, the most suitable scanning conditions can be set with ease. For that reason, in the PCCT apparatus 1 according to the embodiment, the imaging desired by the operator can be achieved under the most suitable scanning conditions, and the examination efficiency (the throughput of the examination) can be enhanced in the photon counting CT scanning of the subject P.

Moreover, in the PCCT apparatus 1 according to the embodiment, an imaging protocol is generated that includes the photon counting CT scanning corresponding to the set scanning conditions. At that time, in the PCCT apparatus 1 according to the embodiment, the imaging protocol includes a plurality of scanning conditions corresponding to a plurality of types of scanning including the photon counting CT scanning. Moreover, in the PCCT apparatus 1 according to the embodiment, during the generation of the imaging protocol, the processing conditions and the reconstruction conditions are set with respect to the data obtained as a result of performing the photon counting CT scanning. For example, in the PCCT apparatus 1 according to the embodiment, a plurality of scanning conditions is set corresponding to a plurality of types of scanning, and at least a single processing condition and at least a single reconstruction condition are set for each type of scanning.

Thus, in the PCCT apparatus 1 according to the embodiment, according to the desired objective of the operator regarding the photon counting CT scanning, the most suitable scanning conditions can be set with ease. As a result, in the PCCT apparatus 1 according to the embodiment, the imaging desired by the operator can be achieved under the most suitable scanning conditions, and the examination efficiency (the throughput of the examination) can be enhanced in the photon counting CT scanning of the subject P.

First Modification Example

According to a first modification example, during the scanning condition setting operation, the specification of the items is performed in order of the target body part for scanning, the imaging mode, and the target material name for imaging in the case in which the material decomposition mode is specified as the imaging mode. That is, in the scanning condition setting operation according to the first modification example, firstly, the operation at Step S402 illustrated in FIG. 4 is performed and that is followed by the operation at Step S401. Subsequently, in place of the operation at Step S403, the specification of the target material name for imaging gets input. Meanwhile, the operation at Step S403 can be performed either at any arbitrary stage before the operation at Step S404 or along with the operation at Step S404.

As a result of implementing the sequence of operations explained above, operation screens related to the specification of the target body part for scanning, the imaging mode, and the target material name for imaging are displayed in order of the target body part for scanning, the imaging mode, and the target material name for imaging in the case in which the material decomposition mode is specified as the imaging mode. When the material name is specified, according to the target body part for scanning and the material name, the scanning condition setting function 445 sets the number of energy ranges and the energy width in each energy range in regard to the energy discrimination of photons in the photon counting CT scanning. At that time, the number of energy ranges and the energy width in each energy range are displayed in an operation screen in the display 42.

In the first modification example, the sequence of operations in the scanning condition setting operation is same as explained above. Moreover, the effects achieved according to the first modification example are identical to the effects achieved according to the embodiment. Hence, that explanation is not given again.

Second Modification Example

According to a second modification example, during the scanning condition setting operation, the specification of the items is performed in order of the target body part for scanning, the X-ray tube voltage, the imaging mode, and the target material name for imaging in the case in which the material decomposition mode is specified as the imaging mode. That is, in the scanning condition setting operation according to the second modification example, firstly, the operation at Step S402 illustrated in FIG. 4 is performed and that is followed by the input of the specification of the X-ray voltage (for example, the peak X-ray tube voltage (kVp)). Subsequently, the operation at Step S401 is performed and that is followed by the input of the specification of the target material name for imaging. Meanwhile, the operation at Step S403 can be performed either at any arbitrary stage before the operation at Step S404 or along with the operation at Step S404.

As a result of implementing the sequence of operations explained above, operation screens related to the specification of the target body part for scanning, the X-ray tube voltage, the imaging mode, and the target material name for imaging are displayed in order of the target body part for scanning, the X-ray tube voltage, the imaging mode, and the target material name for imaging in the case in which the material decomposition mode is specified as the imaging mode. When the material name is specified; according to the target body part for scanning, the X-ray tube voltage, and the material name, the scanning condition setting function 445 sets the number of energy ranges and the energy width in each energy range in regard to the energy discrimination of photons in the photon counting CT scanning. At that time, the number of energy ranges and the energy width in each energy range are displayed in an operation screen in the display 42.

In the second modification example, the sequence of operations in the scanning condition setting operation is same as explained above. Moreover, the effects achieved according to the second modification example are identical to the effects achieved according to the embodiment. Hence, that explanation is not given again.

Third Modification Example

According to a third modification example, during the scanning condition setting operation, the specification of the items is performed in order of the imaging mode, the target body part for scanning, and the target material name for imaging in the case in which the material decomposition mode is specified as the imaging mode. That is, in the scanning condition setting operation according to the third modification example, firstly, the operations at Step S401 and S402 illustrated in FIG. 4 are performed, and those are followed by the input of the specification of the target material name for imaging. Meanwhile, the operation at Step S403 can be performed either at any arbitrary stage before the operation at Step S404 or along with the operation at Step S404.

As a result of implementing the sequence of operations explained above, operation screens related to the specification of the imaging mode, the target body part for scanning, and the target material name for imaging are displayed in order of the imaging mode, the target body part for scanning, and the target material name for imaging in the case in which the material decomposition mode is specified as the imaging mode. When the material name is specified, according to the target body part for scanning and the material name, the scanning condition setting function 445 sets the number of energy ranges and the energy width in each energy range in regard to the energy discrimination of photons in the photon counting CT scanning. At that time, the number of energy ranges and the energy width in each energy range are displayed in an operation screen in the display 42.

In the third modification example, the sequence of operations in the scanning condition setting operation is same as explained above. Moreover, the effects achieved according to the third modification example are identical to the effects achieved according to the embodiment. Hence, that explanation is not given again.

Fourth Modification Example

According to a fourth modification example, during the scanning condition setting operation, the specification of the items is performed in order of the imaging mode, the X-ray tube voltage, and the target material name for imaging in the case in which the material decomposition mode is specified as the imaging mode. That is, in the scanning condition setting operation according to the fourth modification example, firstly, the operations at Step S401 and S402 illustrated in FIG. 4 are performed, and those are followed by the input of the specification of the X-ray tube voltage (for example, the peak X-ray tube voltage (kVp)). Subsequently, the operation at Step S401 is performed and that is followed by the input of the specification of the target material name for imaging. Meanwhile, the operation at Step S403 can be performed either at any arbitrary stage before the operation at Step S404 or along with the operation at Step S404.

As a result of implementing the sequence of operations explained above, operation screens related to the specification of the imaging mode, the target body part for scanning, the X-ray tube voltage, and the target material name for imaging are displayed in order of the target body part for scanning, the X-ray tube voltage, the imaging mode, and the target material name for imaging in the case in which the material decomposition mode is specified as the imaging mode. When the material name is specified; according to the target body part for scanning, the X-ray tube voltage, and the material name, the scanning condition setting function 445 sets the number of energy ranges and the energy width in each energy range in regard to the energy discrimination of photons in the photon counting CT scanning. At that time, the number of energy ranges and the energy width in each energy range are displayed in an operation screen in the display 42.

In the fourth modification example, the sequence of operations in the scanning condition setting operation is same as explained above. Moreover, the effects achieved according to the fourth modification example are identical to the effects achieved according to the embodiment. Hence, that explanation is not given again.

First Application Example

In a first application example, the scanning conditions are set according to the examination objective of examining the subject P using the photon counting CT scanning. That is, according to the embodiment and the first application example, in the PCCT apparatus 1, based on the imaging mode related to the photon counting CT scanning or based on the examination objective of examining the subject P using the photon counting CT scanning, the required scanning conditions in the photon counting CT scanning are set and are displayed in the display 42. Herein, the examination objective is, for example, a disease name regarding the subject P.

The scanning condition setting function 445 of the processing circuitry 44 sets the required scanning conditions in the photon counting CT scanning according to the examination objective (can also be referred to as the clinical aim) for the subject P using the photon counting CT scanning. Hereinafter, in order to make the explanation more specific, brain infarction is assumed to the examination objective for the subject P. In the case of brain infarction or cardiac infarction, for example, the usage of a contrast agent is set. If cardiac infarction represents the examination objective, then the scanning conditions (the bin count and the energy bins) related to the discrimination of calcium, which represents the material name in the material decomposition mode, is preset. Alternatively, if a kidney stone represents the examination objective, then the scanning conditions (the bit count and the energy bins) corresponding to the calcium series or a non-calcium series (magnesium) are preset.

In the PCCT apparatus 1, an examination order for the subject P is received from, for example, a radiology information system (RIS) via a communication interface (not illustrated). The scanning condition setting function 445 of the processing circuitry 44 identifies the examination objective specified in the examination order. If brain infarction represents the examination objective, then the scanning condition setting function 445 selects the head region as the target body part for scanning.

Moreover, the scanning condition setting function 445 of the processing circuitry 44 sets a predetermined X-ray tube voltage that is associated in advance to the target body part for scanning and the disease name. The association is stored, in the memory 41, as look up tables including the X-ray tube voltage with respect to the target body part for scanning and the disease name, the presence or absence of a contrast agent, and the type of the contrast agent. The scanning condition setting function 445 collates the examination objective with the look up table and, for example, sets a contrast agent of the iodine series. Moreover, the scanning condition setting function 445 collates the head region, the presence of a contrast agent of the iodine series, and the predetermined X-ray tube with the look up tables according to the embodiment, and accordingly sets the scanning conditions.

Then, the scanning condition setting function 445 of the processing circuitry 44 displays the scanning conditions in the display 42. From among the scanning conditions displayed in the display 42, if the material name included in the contrast agent is changed according to an instruction issued by the operator via the input interface 43, then the scanning condition setting function 445 changes the scanning conditions according to the changed material name.

For example, from among the scanning conditions displayed in the display 42, if the specification for the contrast agent is changed from a contrast agent of the iodine series to a contrast agent of the gadolinium series, then the scanning condition setting function 445 sets a change proposal for changing the scanning conditions according to gadolinium, and displays the change proposal, that is, displays the changed scanning conditions in the display 42. At that time, in the change proposal, in addition to changing the bin count and the width of the energy bins according to gadolinium, the X-ray tube current can also be changed.

Meanwhile, regarding the display of the changed scanning conditions in the display 42, the changed portion can be displayed with reference to the set scanning conditions. At that time, when an instruction for confirming the changed portion (also called a finalization instruction) is input by the operator via the input interface 43, the scanning condition setting function 445 displays, in the display 42, the scanning conditions corresponding to the change proposal.

As a response to the finalization instruction issued by the operator regarding the scanning conditions; based on the target body part for scanning, the contrast agent, the X-ray tube voltage, the material name, the imaging mode, and the inspection objective, the scanning condition setting function 445 sets an imaging protocol name different than the other imaging protocols. With that, the scanning condition setting function 445 stores, in the memory 41, the scanning conditions, which correspond to the finalization instruction, and the imaging protocol name in a corresponding manner. Moreover, the scanning conditions can also be incorporated in the look up table in a corresponding manner to the imaging protocol name.

In the scanning condition setting operation according to the first application example, instead of performing the operations from Step S401 to Step S404 illustrated in FIG. 4, the scanning conditions are set according to the examination objective. Moreover, at Step S406, an imaging protocol name is set according to the finalized imaging protocol. Meanwhile, in the first application example, the sequence of operations in the scanning condition setting operation is same as explained above. Moreover, the effects achieved according to the first application example are identical to the effects achieved according to the embodiment. Hence, that explanation is not given again.

Second Application Example

In a second application example, the scanning conditions are set at the time of generating an imaging protocol. In the scanning condition setting operation according to the second application example, instead of performing the operations from Step S401 to Step S404, the scanning conditions are set based on the examination order.

For example, at the time of editing the imaging protocol, the scanning condition setting function 445 of the processing circuitry 44 selects a plurality of predetermined scanning conditions based on the examination order output from an RIS and, according to the correction of the selected scanning conditions as made by the operator, sets the scanning conditions performed in the photon counting CT scanning. That is, immediately before the scanning of the subject P, according to an instruction issued by the operator based on, for example, the examination order for the subject P as output from an RIS (i.e., according to a user input done while checking the examination order); the scanning condition setting function 445 selects, from a plurality of preset scanning conditions, the scanning conditions to be used in the scanning of the subject P.

The scanning condition setting function 445 of the processing circuitry 44 finalizes the scanning conditions according to the correction of the selected scanning conditions as made by the user. The protocol generation function 446 of the processing circuitry 44 generates an imaging protocol that includes the photon counting CT scanning corresponding to the set scanning conditions.

Prior to the execution of the scanning condition setting operation, a plurality of predetermined scanning conditions is set by the user (for example, a radiology technologist or a service person) and is stored in the memory 41. For example, the scanning condition setting function 445 of the processing circuitry 44 sets a plurality of predetermined scanning conditions based on the input of the operator according to a plurality of examination objectives. Those predetermined scanning conditions are stored in the memory 41. Meanwhile, the user can additionally perform further setting about the predetermined scanning conditions.

Prior to the execution of the scanning condition setting operation, the protocol generation function 446 of the processing circuitry 44 uses the predetermined scanning conditions that are set and, as may be necessary, generates (presets) a predetermined imaging protocol that includes the photon counting CT scanning. The generation of a preset imaging protocol is performed by the user using, for example, an operation screen (a user interface) that is identical to the screen used for editing the imaging protocol. The predetermined imaging protocol is then stored in the memory 41 for use in the scanning condition setting operation. For example, the predetermined imaging protocol is used in setting an imaging protocol for the subject P. Meanwhile, the user can additionally perform further setting about the predetermined scanning conditions.

In the second application example, the sequence of operations in the scanning condition setting operation is same as explained above. Moreover, the effects achieved according to the second application example are identical to the effects achieved according to the embodiment. Hence, that explanation is not given again.

Third Application Example

In a third application example, during the generation of an imaging protocol, if any different reconstruction conditions are added, then the protocol generation function 446 adjusts the set scanning conditions and the set reconstruction conditions, and determines whether or not medical images can be generated by performing reconstruction processing according to the different reconstruction conditions. Hereinafter, in order to make the explanation more specific, it is assumed that the imaging protocol being generated includes scanning conditions with brain infarction as the examination objective. At that time, the head region is set as the target body part for scanning.

During the generation of an imaging protocol as explained at Step S407 illustrated in FIG. 4, according to an instruction issued by the operator via the input interface 43, a different image generation condition regarding the head region is added. Assume that the added image generation condition is, for example, a condition for generating a medical image (a material decomposition image) enabling discrimination (recognition) of particular materials (the white matter of the brain and the gray matter of the brain). In that case, the protocol generation function 446 of the processing circuitry 44 determines whether a medical image to be generated according to the different image generation condition can be generated as a result of adjusting the scanning conditions (for example, the manner of dividing (partitioning) a plurality of energy bins and/or the weighting of the data obtained in a plurality of energy bins), adjusting the reconstruction conditions, and performing the already-set type of scanning once; or whether it is required to perform the scanning twice.

The criterion for the determination performed by the protocol generation function 446 is, for example, whether the setting about the energy bins, such as the manner of dividing a plurality of energy bins in which the brain infarction (mainly visualization of the blood vessels using a contrast agent) can be highlighted and/or the range of the energy bins, can coexist with the setting about the energy bins in which some other specific material can be highlighted. The protocol generation function 446 collates that criterion and if, for example, the situation is such that the bin count is not sufficient to highlight the two concerned materials, determines that the medical images cannot be generated by performing the scanning only once.

If it is determined that the medical images can be generated (hereinafter, called generatability determination), then the protocol generation function 446 of the processing circuitry 44 adjusts the set scanning conditions and the set reconstruction conditions and generates an imaging protocol. Moreover, using the generatability determination, in which it is determined that different images related to different reconstruction conditions can coexist, as a trigger; the protocol generation function 446 can integrate (combine), if possible, the imaging protocol related to the different reconstruction conditions and the imaging protocol that includes the pre-adjustment scanning conditions and the pre-adjustment reconstruction conditions. That is, in response to the generatability determination, the protocol generation function 446 integrates the imaging protocol that includes the set scanning conditions and the set reconstruction conditions with the imaging protocol that includes different reconstruction conditions.

In the third application example, the sequence of operations in the scanning condition setting operation is same as explained above. Moreover, the effects achieved according to the third application example are identical to the effects achieved according to the embodiment. Hence, that explanation is not given again.

Fourth Application Example

In a fourth application example, the third application example is implemented at the time of newly creating an imaging protocol. For example, in the setting of the scanning conditions and the setting of the imaging protocol, a plurality of materials can be made specifiable with respect to a single target body part for scanning and, according to the determination about whether or not simultaneous detection of a plurality of materials is possible, it is determined whether or not to specify, in the imaging protocol, about performing the photon counting CT scanning once.

In the setting of the scanning condition, when the material decomposition mode is set as the imaging mode, the scanning condition setting function 445 of the processing circuitry 44 sets a plurality of material name s to be specifiable with respect to a single target body part for scanning in the photon counting CT scanning. That is, after the material decomposition mode is set, the scanning condition setting function 445 displays, in the display 42, an operation screen in which a plurality of material name s can be specified. In the operation screen, the input of a plurality of material names is performed according to an instruction issued by the operator via the input interface. Herein, the scanning condition setting function 445 performs operations after, for example, the operation at Step S402 illustrated in FIG. 4.

The protocol generation function 446 of the processing circuitry 44 adjusts the set scanning conditions and the set reconstruction conditions, and determines whether or not a plurality of materials corresponding to a plurality of material names is simultaneously detectible. That is, the protocol generation function 446 adjusts the scanning conditions and the reconstruction conditions and determines whether or not medical images related to the specified materials can be generated. If it is determined that a plurality materials can be detected, then the protocol generation function 446 adjusts the set scanning conditions and the set reconfiguration conditions, and generates an imaging protocol related to a single iteration of scanning. Herein, the protocol generation function 446 performs the operations at Step S405 illustrated in FIG. 4.

In the fourth application example, the sequence of operations in the scanning condition setting operation is same as explained above. Moreover, the effects achieved according to the fourth application example are identical to the effects achieved according to the embodiment. Hence, that explanation is not given again.

Fifth Application Example

In a fifth application example, an operation screen is displayed when the photon counting mode is specified as the imaging mode. In the scanning condition setting operation according to the fifth application example, at Step S401, the photon counting mode is specified as the imaging mode according to a user instruction issued via the input interface 43. At that time, at Step S402, the scanning condition setting function 445 of the processing circuitry 44 displays, in the display 42, an operation screen related to the setting of the presence or absence of a contrast agent and/or the setting of the target body part for scanning in the photon counting CT scanning.

Then, at Step S403, according to the presence or absence of a contrast agent and/or the target body part for scanning in the photon counting CT scanning, the scanning condition setting function 445 of the processing circuitry 44, displays, in the display 42, an operation screen related to the specification of: the X-ray tube voltage (the voltage value of the X-ray tube voltage or the peak X-ray tube voltage (kilovolts peak (kVp)); the number of a plurality of energy ranges related to the energy discrimination of the photons in the photon counting CT scanning; and the energy width in the energy range. The subsequent operations are identical to the operations according to the embodiment. Hence, that explanation is not given again. Moreover, in the fifth modification example, the sequence of operations in the scanning condition setting operation is same as explained above.

In the PCCT apparatus 1 according to the fifth application example, when the photon counting mode is specified as the imaging mode, according to the presence or absence of a contrast agent and/or the target body part for scanning in the photon counting CT scanning, operation screens are displayed in regard to the specification of the X-ray tube voltage, the number of energy ranges related to the energy discrimination of the photons in the photon counting CT scanning, and the energy width in the energy range. As a result, in the PCCT apparatus 1 according to the fifth application example, according to the contrast agent and the target body part for imaging, the energy bands of interest (the energy bins of interest) can be collected in detail, and the weight of the count of the energy bands (the energy bins) in the postprocessing can be changed. For that reason, in the PCCT apparatus 1 according to the fifth application example, although the CT images are close to the conventional CT images, it becomes possible to enhance the visibility of the material and/or the body part of interest for the operator. For example, it becomes possible to enhance the contrast. Meanwhile, the other effects achieved according to the fifth application example are identical to the effects achieved according to the embodiment. Hence, that explanation is not given again.

When the technical idea according to the embodiment is to be implemented using a photon-counting CT-scanning condition setting method; in the photon-counting CT-scanning condition setting method, based on the imaging mode related to the photon counting CT scanning, the required scanning conditions are set in the photon counting CT scanning explained above. The sequence and the effects of the scanning condition setting operation in the photon-counting CT-scanning condition setting method are identical to the embodiment. Hence, that explanation is not given again.

When the technical idea according to the embodiment is to be implemented in a photon-counting CT-scanning condition setting apparatus; the photon-counting CT-scanning condition setting apparatus includes a scanning condition setting unit that, based on the imaging mode related to the photon counting CT scanning, sets the required scanning conditions in the photon counting CT scanning. The photon-counting CT-scanning condition setting apparatus is implemented using, for example, a tablet terminal capable of performing wireless communication with various servers, an RIS terminal, and/or the console apparatus 40. The sequence and the effects of the scanning condition setting operation performed in the photon-counting CT-scanning condition setting apparatus are identical to the embodiment. Hence, that explanation is not given again.

When the technical idea according to the embodiment is to be implemented using a photon-counting CT-scanning condition setting program; the photon-counting CT-scanning condition setting program causes a computer to set the required scanning conditions in the photon counting CT scanning based on the imaging mode related to the photon counting CT scanning explained above. The photon-counting CT-scanning condition setting program is stored in, for example, a computer-readable nonvolatile memory medium.

Alternatively, for example, the photon-counting CT-scanning condition setting program can be installed in a server device (processing device), which is involved in medical data processing, from a nonvolatile memory medium. Then, the photon-counting CT-scanning condition setting program can be loaded in the memory, and the scanning condition setting operation can be implemented. At that time, the computer program enabling a computer to implement the concerned method can also be stored in and distributed via a memory medium such as a magnetic disk (a hard disk), an optical disc (a CD-ROM or a DVD), or a semiconductor memory. The sequence and the effects of the photon-counting CT-scanning condition setting program are identical to the embodiment. Hence, that explanation is not given again.

According to at least one of the aspects of the embodiment described above, in the CT examination performed using the PCCT apparatus 1, it can be ensured that the radiographic conditions are set in the most suitable manner.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In regard to the embodiment described above, following notes are disclosed as an aspect of the invention and as selective features.

(Note 1)

A photon counting computed tomography apparatus includes:

a scanning condition setting unit configured to set a scanning condition required in photon counting CT scanning based on the imaging mode related to photon counting CT scanning or based on the examination objective of performing the photon counting CT scanning of a subject; and a display configured to display the set scanning condition.

(Note 2)

The display can be configured to display an operation screen in which the items in a plurality of elements related to the setting of the scanning condition are specifiable according to a predetermined order, and the scanning condition setting unit can be configured to set the scanning condition using the items in the elements that are input via the operation screen.

(Note 3)

The imaging mode can include a photon counting mode and a material decomposition mode, and the plurality of elements represent at least two elements from among the type of the imaging mode, the target body part for scanning in the photon counting CT scanning, the presence or absence of a contrast agent, the type of the contrast agent, the X-ray tube voltage, and the material name in the material decomposition mode.

(Note 4)

The display unit is configured to display, in order, the operation screen related to: specification of the type of imaging mode; the target body part for scanning; presence or absence of a contrast agent; and type of the contrast agent, and when the material decomposition mode is specified as the imaging mode and when the presence or absence of a contrast agent and the type of the contrast agent are specified, according to the target body part for scanning and according to the presence or absence of a contrast agent and the type of the contrast agent, the display unit is configured to display the number of energy ranges related to energy discrimination of photons in the photon counting CT scanning and the energy width in the energy ranges in the operation screen.

(Note 5)

The display unit is configured to display, in order, the operation screen related to: the target body part for scanning, the imaging mode, and the material name in the case in which the material decomposition mode is specified as the imaging mode, and when the material name is specified, according to the target body part for scanning and the material name, the display unit is configured to display the number of the energy ranges related to energy discrimination of photons in the photon counting CT scanning and the energy width in the energy ranges in the operation screen.

(Note 6)

The display unit is configured to display, in order, the operation screen related to: the target body part for scanning, the X-ray tube voltage, the imaging mode, and the material name in the case in which the material decomposition mode is specified as the imaging mode, and when the material name is specified, according to the target body part for scanning, the X-ray tube voltage, and the material name, the display unit is configured to display the number of energy ranges related to energy discrimination of photons in the photon counting CT scanning and the energy width in the energy ranges in the operation screen.

(Note 7)

The display unit is configured to display, in order, the operation screen related to: the imaging mode, the target body part for scanning, and the material name in the case in which the material decomposition mode is specified as the imaging mode, and when the material name is specified, according to the target body part for scanning and the material name, the display unit is configured to display the number of energy ranges related to energy discrimination of photons in the photon counting CT scanning and the energy width in the energy ranges in the operation screen.

(Note 8)

The display unit (42) is configured to display, in order, the operation screen related to: the imaging mode, the target body part for scanning, the X-ray tube voltage, and the material name in the case in which the material decomposition mode is specified as the imaging mode, and when the material name is specified, according to the target body part for scanning, the X-ray tube voltage, and the material name, the display unit is configured to display the number of energy ranges related to energy discrimination of photons in the photon counting CT scanning and the energy width in the energy ranges in the operation screen.

(Note 9)

When the photon counting mode is specified as the imaging mode, according to the presence or absence of a contrast agent and/or according to the target body part for scanning in the photon counting CT scanning, the display unit can be configured to display the operation screen related to the specification of the X-ray tube voltage, the number of energy ranges related to energy discrimination of photons in the photon counting CT scanning, and the energy width in the energy ranges.

(Note 10)

In the displayed scanning condition, when the material name included in the contrast agent is changed, the scanning condition setting unit can change the scanning condition according to the changed material name, and the display can be configured to display the changed scanning condition.

(Note 11)

The scanning condition setting unit (445) is configured to set an imaging protocol having a different name than other imaging protocol in response to a finalization instruction issued by an operator for finalizing the scanning condition, based on the target body part for scanning, the contrast agent, the X-ray tube voltage, the material name, the imaging mode, and the examination objective that are specified in the scanning condition corresponding to the finalization instruction.

(Note 12)

The imaging mode can include a photon counting mode and a material decomposition mode, and when the photon counting mode is selected as the imaging mode, based on the count data obtained as a result of performing the photon counting CT scanning, the scanning condition setting unit can be configured to reconstruct an integral image corresponding to the energy integral of the detected photons.

(Note 13)

A photon-counting CT-scanning condition setting method includes setting a scanning condition required in the photon counting CT scanning based on the imaging mode related to photon counting CT scanning or based on the examination objective of performing the photon counting CT scanning of a subject.

(Note 14)

A photon counting computed tomography apparatus includes:

a scanning condition setting unit configured to select a plurality of predetermined scanning conditions based on an examination order output from a radiology information system and, according to the correction made in the selected scanning conditions by the operator, configured to set scanning conditions to be implemented in photon counting CT scanning; and a protocol generating unit configured to generate an imaging protocol which includes the photon counting CT scanning corresponding to the set scanning conditions.

(Note 15)

The scanning condition setting unit can be configured to set the predetermined scanning conditions based on inputs from the operator according to a plurality of examination objectives, and the protocol generating unit can be configured to use the predetermined scanning conditions and generate a predetermined imaging protocol that includes the photon counting CT scanning.

(Note 16)

The imaging protocol can be configured to include a plurality scanning conditions corresponding to a plurality of types of scanning including the photon counting CT scanning.

(Note 17)

At the time of generating the imaging protocol, the protocol generating unit can be configured to set processing conditions and reconstruction conditions with respect to the data obtained as a result of performing the photon counting CT scanning.

(Note 18)

The scanning condition setting unit can be configured to set a plurality of scanning conditions with respect to the plurality of types of scanning, and regarding each of the plurality of types of scanning, the protocol generating unit can be configured to set at least one of the processing conditions and at least one of the reconstruction conditions.

(Note 19)

During the generation of the imaging protocol, when a different reconstruction condition is added, the protocol generating unit can be configured to adjust the set scanning conditions and the set reconstruction conditions, and can be configured to determine whether or not it is possible to generate a medical image reconstructed according to the different reconstruction condition.

(Note 20)

When it is determined that the medical image can be generated, the protocol generating unit can be configured to integrate the imaging protocol including the set scanning conditions and the set reconstruction conditions with the imaging protocol including the different reconstruction condition.

(Note 21)

In the setting of the scanning condition, when the material decomposition mode is set as the imaging mode, the scanning condition setting unit can be configured to perform setting to enable specification of a plurality of material names with respect to a single target body part for scanning in the photon counting CT scanning, and the protocol generating unit can be configured to adjust the set scanning condition and the set reconstruction condition and determine whether or not a plurality of materials corresponding to the plurality of material names is simultaneously detectible, and when it is determined that the plurality of materials are detectible, can be configured to adjust the set scanning conditions and the set reconstruction conditions, and generate an imaging protocol regarding the one type of scanning.

(Note 22)

The display unit can be configured to display, in order, the operation screen related to specification of type of the imaging mode, the target body part for scanning, the presence or absence of a contrast agent, and type of the contrast agent.

(Note 23)

The display unit can be configured to display, in order, the operation screen related to: the target body part for scanning, the imaging mode, and the material name in case in which the material decomposition mode is specified as the imaging mode.

(Note 24)

The display unit can be configured to display, in order, the operation screen related to: the target body part for scanning, the X-ray tube voltage, the imaging mode, and the material name in case in which the material decomposition mode is specified as the imaging mode.

(Note 25)

The display unit can be configured to display, in order, the operation screen related to: the imaging mode, the target body part for scanning, and the material name in case in which the material decomposition mode is specified as the imaging mode.

(Note 26)

The display unit can be configured to display, in order, the operation screen related to: the imaging mode, the target body part for scanning, the X-ray tube voltage, and the material name in case in which the material decomposition mode is specified as the imaging mode.

(Note 27)

The display can be configured to display the operation screen related to specification of X-ray tube voltage, number of a plurality of energy ranges related to energy discrimination of photons in the photon counting CT scanning, and energy width in the energy ranges.

What is claimed is:

1. A photon counting computed tomography apparatus comprising:

processing circuitry configured to set a scanning condition required in a photon counting CT scanning based on an imaging mode related to the photon counting CT scanning or based on an examination objective of performing the photon counting CT scanning of a subject, wherein the scanning condition includes a condition for counting a number of photons without discriminating photon energies; and a display configured to display the scanning condition.

2. The photon counting computed tomography apparatus according to claim 1, wherein the display is further configured to display an operation screen in which items in a plurality of elements related to setting of the scanning condition are specifiable according to a predetermined order, and the processing circuitry is further configured to set the scanning condition using items in the elements that are input via the operation screen.

3. The photon counting computed tomography apparatus according to claim 2, wherein the imaging mode includes a photon counting mode and a material decomposition mode, and the plurality of elements represent at least two elements from among a type of the imaging mode, a target body part for scanning in the photon counting CT scanning, presence or absence of a contrast agent, a type of the contrast agent, an X-ray tube voltage, and a material name in the material decomposition mode.

4. The photon counting computed tomography apparatus according to claim 3, wherein the display is further configured to display, in order, the operation screen related to a specification of the type of imaging mode, the target body part for scanning, presence or absence of a contrast agent, and type of the contrast agent, and when the material decomposition mode is specified as the imaging mode and when the presence or absence of the contrast agent and the type of the contrast agent are specified, according to the target body part for scanning and according to the presence or absence of the contrast agent and the type of the contrast agent, the display is further configured to display a number of a plurality of energy ranges related to energy discrimination of photons in the photon counting CT scanning and an energy width in the energy ranges in the operation screen.

5. The photon counting computed tomography apparatus according to claim 3, wherein the display is further configured to display, in order, the operation screen related to the target body part for scanning, the imaging mode, and the material name in case in which the material decomposition mode is specified as the imaging mode, and when the material name is specified, according to the target body part for scanning and the material name, the display is further configured to display a number of a plurality of energy ranges related to energy discrimination of photons in the photon counting CT scanning and an energy width in the energy ranges in the operation screen.

6. The photon counting computed tomography apparatus according to claim 3, wherein the display is further configured to display, in order, the operation screen related to: the target body part for scanning, the X-ray tube voltage, the imaging mode, and the material name in case in which the material decomposition mode is specified as the imaging mode, and when the material name is specified, according to the target body part for scanning, the X-ray tube voltage, and the material name, the display is further configured to display a number of a plurality of energy ranges related to energy discrimination of photons in the photon counting CT scanning and an energy width in the energy ranges in the operation screen.

7. The photon counting computed tomography apparatus according to claim 3, wherein the display is further configured to display, in order, the operation screen related to the imaging mode, the target body part for scanning, and the material name in case in which the material decomposition mode is specified as the imaging mode, and when the material name is specified, according to the target body part for scanning and the material name, the display is further configured to display a number of a plurality of energy ranges related to energy discrimination of photons in the photon counting CT scanning and an energy width in the energy ranges in the operation screen.

8. The photon counting computed tomography apparatus according to claim 3, wherein the display is further configured to display, in order, the operation screen related to the imaging mode, the target body part for scanning, the X-ray tube voltage, and the material name in case in which the material decomposition mode is specified as the imaging mode, and when the material name is specified, according to the target body part for scanning, the X-ray tube voltage, and the material name, the display is further configured to display a number of a plurality of energy ranges related to energy discrimination of photons in the photon counting CT scanning and an energy width in the energy ranges in the operation screen.

9. The photon counting computed tomography apparatus according to claim 4, wherein, when the photon counting mode is specified as the imaging mode, according to the presence or absence of the contrast agent and/or according to the target body part for scanning in the photon counting CT scanning, the display is further configured to display the operation screen related to a specification of the X-ray tube voltage, the number of a plurality of energy ranges related to energy discrimination of photons in the photon counting CT scanning, and the energy width in the energy ranges.

10. The photon counting computed tomography apparatus according to claim 1, wherein in the displayed scanning condition, when a material name included in a contrast agent is changed, the processing circuitry is further configured to change the scanning condition according to the changed material name, and the display is further configured to display the changed scanning condition.

11. The photon counting computed tomography apparatus according to claim 10, wherein the processing circuitry is further configured to set an imaging protocol having a name that is different from another imaging protocol in response to a finalization instruction issued by an operator for finalizing the scanning condition, based on a target body part for scanning, the contrast agent, an X-ray tube voltage, the material name, the imaging mode, and the examination objective that are specified in scanning condition corresponding to the finalization instruction.

12. The photon counting computed tomography apparatus according to claim 1, wherein the imaging mode includes a photon counting mode and a material decomposition mode, and when the photon counting mode is selected as the imaging mode, based on count data obtained as a result of performing the photon counting CT scanning, the processing circuitry is further configured to reconstruct an integral image corresponding to energy integral of detected photons.

13. A photon-counting CT-scanning condition setting method comprising:

setting a scanning condition required in a photon counting CT scanning based on an imaging mode related to the photon counting CT scanning or based on an examination objective of performing the photon counting CT scanning of a subject, wherein the scanning condition includes a condition for counting a number of photons without discriminating photon energies; and displaying the scanning condition.

* * * * *